(12) United States Patent
Dey et al.

(10) Patent No.: US 11,183,308 B2
(45) Date of Patent: *Nov. 23, 2021

(54) ESTIMATING PERSONALIZED DRUG RESPONSES FROM REAL WORLD EVIDENCE

(71) Applicant: International Business Machines Corporation, Armonk, NY (US)

(72) Inventors: Sanjoy Dey, White Plains, NY (US); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 214 days.

This patent is subject to a terminal disclaimer.

(21) Appl. No.: 16/209,196

(22) Filed: Dec. 4, 2018

(65) Prior Publication Data
US 2019/0198179 A1   Jun. 27, 2019

Related U.S. Application Data

(63) Continuation of application No. 15/855,314, filed on Dec. 27, 2017, now Pat. No. 11,107,589.

(51) Int. Cl.
*G16H 70/40* (2018.01)
*G16H 10/60* (2018.01)
(Continued)

(52) U.S. Cl.
CPC ............ *G16H 70/40* (2018.01); *G16H 10/60* (2018.01); *G16H 20/10* (2018.01); *G16H 50/20* (2018.01); *G16H 50/70* (2018.01); *G06F 16/93* (2019.01)

(58) Field of Classification Search
None
See application file for complete search history.

(56) References Cited

U.S. PATENT DOCUMENTS

| 6,317,731 | B1 * | 11/2001 | Luciano ............... | G16H 50/50 |
| | | | | 706/21 |
| 2012/0041772 | A1 * | 2/2012 | Ebadollahi ............ | G16H 50/20 |
| | | | | 705/2 |

FOREIGN PATENT DOCUMENTS

WO   WO-2017059022 A1 *   4/2017   ............. G16H 50/50

OTHER PUBLICATIONS

Bertsimas et al., Personalized Diabetes Management Using Electronic Medical Records, Feb. 2017, Diabetes Care, vol. 40, pp. 210-217, DOI: 10.2337/dc16-0826 (Year: 2017).*

(Continued)

*Primary Examiner* — Devin C Hein
(74) *Attorney, Agent, or Firm* — Stephen R. Tkacs; Stephen J. Walder, Jr.; William J. Stock

(57) ABSTRACT

A mechanism is provided in a data processing system comprising at least one processor and at least one memory, the at least one memory comprising instructions executed by the at least one processor to cause the at least one processor to implement a drug response estimation engine. The drug response estimation engine receives real-world evidence for a plurality of patients. A patient similarity network builder component executing within the drug response estimation engine builds a patient similarity network. A regression analysis component executing within the drug response estimation engine builds a network localized regression analysis approach. A patient clustering component executing within the drug response estimation engine groups patients based on demographics and comorbidities to form a plurality of patient clusters. The drug response estimation engine estimates drug responses for a given patient based on the patient similarity network, the network localized regression analysis approach, and the plurality of patient clusters. The (Continued)

drug response estimation engine outputs the drug responses for the given patient.

20 Claims, 5 Drawing Sheets

(51) Int. Cl.
*G16H 50/20* (2018.01)
*G16H 20/10* (2018.01)
*G16H 50/70* (2018.01)
G06F 16/93 (2019.01)

(56) References Cited

OTHER PUBLICATIONS

Yamada et al, Localized Lasso for High-Dimensional Regression, Oct. 17, 2016, arXiv:1603.06743 (Year: 2016).*
List of IBM Patents or Patent Applications Treated as Related, Dec. 4, 2018, 2 pages.

* cited by examiner

FIG. 5

Algorithm 1 Iteratively Reweighted Least Squares for localized lasso regularization 1: Input: $Z, y, D, R, \lambda_1, \lambda_2$
2: Data: $W$
3: $t \leftarrow 0$. Initialize $H^{(0)}$
4: repeat
5:     $k \leftarrow k + 1$
6:     while stopping criteria not met do
7:         $W^{(t+1)} \leftarrow (H^{(t)})^{-1} Z^\top D^\top (I_n + DZ(H^{(t)})^{-1} Z^\top D^\top)^{-1} Dy$
8:         Compute $H^{(t+1)}$ based on $W^{(t+1)}$
9:         $t \leftarrow t + 1$
10:    end while
11: until stopping criteria not met

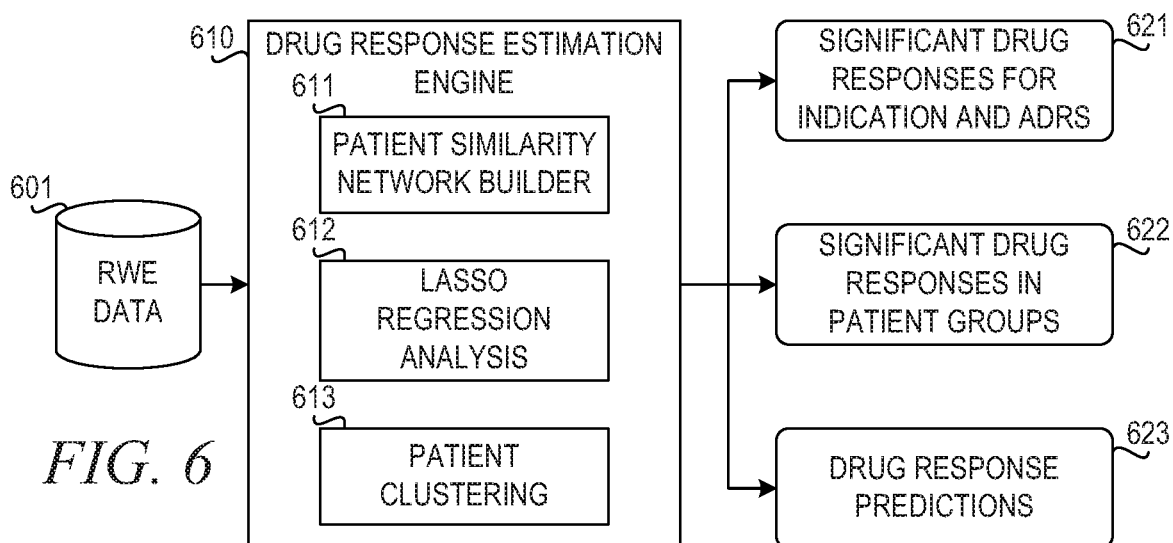

FIG. 6

ESTIMATING PERSONALIZED DRUG RESPONSES FROM REAL WORLD EVIDENCE

BACKGROUND

The present application relates generally to an improved data processing apparatus and method and more specifically to mechanisms for estimating personalized drug responses from real world evidence.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions executed by the at least one processor to cause the at least one processor to implement a drug response estimation engine. The drug response estimation engine operates to receive real-world evidence for a plurality of patients. A patient similarity network builder component executing within the drug response estimation engine builds a patient similarity network. A regression analysis component executing within the drug response estimation engine builds a network localized regression analysis approach. A patient clustering component executing within the drug response estimation engine groups patients based on demographics and comorbidities to form a plurality of patient clusters. The drug response estimation engine estimates drug responses for a given patient based on the patient similarity network, the network localized regression analysis approach, and the plurality of patient clusters. The drug response estimation engine outputs the drug responses for the given patient.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 5 depicts an algorithm for iteratively reweighted least squares for localized lasso regularization in accordance with an illustrative embodiment;

FIG. 6 is a block diagram illustrating a drug response estimation engine in accordance with an illustrative embodiment.

DETAILED DESCRIPTION

Figure 1:
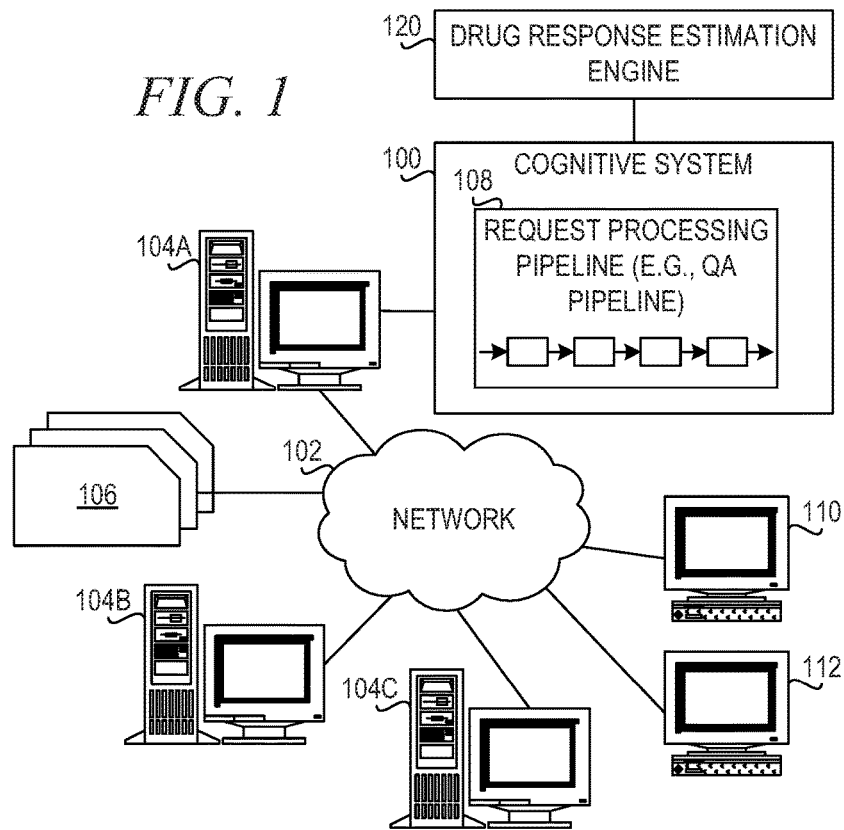
FIG. 1 depicts a schematic diagram of one illustrative embodiment of a cognitive healthcare system in a computer network.

The strengths of current cognitive systems, such as current medical diagnosis, patient health management, patient treatment recommendation systems, law enforcement investigation systems, and other decision support systems, are that they can provide insights that improve the decision making performed by human beings. For example, in the medical context, such cognitive systems may improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of applications as well as more representative of the way in which human beings make decisions, such as diagnosing and treating patients. In particular, one drawback of current systems is that not all patients in a patient group or cohort have similar responses to drugs. Thus, while patient cohort analysis may provide a general recommendation as to drug treatment options for patients in order to provide proper treatment of individual patients within the cohort, it is important to take into consideration their own personal characteristics and potential for adverse drug reactions (ADRs) to the drug options. This is a precision medicine problem.

Predicting the responses of drugs, both positive (e.g., therapeutic effects) and negative (e.g., adverse drug reactions (ADRs)) is an important problem for finding new effective and safe drugs. Real-world evidence (e.g., electronic medical records (EMRs), claims) can be used for finding drug responses that were not considered and/or tested during the drug design phase. Furthermore, a drug might have heterogeneous effects on different patients. Estimating the personalized effects of different drugs on different patients is important for personalized and precise medicine. Previous approaches to finding drug responses from real-world evidence are mostly on a global scale, i.e., they consider all patients together and, thus, are not able to predict the responses of drugs for an individual patient.

The illustrative embodiments provide mechanisms for estimating personalized drug responses from real world evidence. The illustrative embodiments leverage baseline regularization framework for finding the responses of drugs for a particular outcome (e.g., lab tests change, adverse drug reactions happen). Moreover, the illustrative embodiments provide personalized drug response estimation from real-world evidence based on localized LASSO regression analysis built on patient similarities.

In contrast to the one-size-fits-all medicine, personalized medicine aims to tailor treatment to the individual characteristics of each patient. This requires the ability to classify patients into subgroups with predictable response to a specific treatment. Although there are already many examples of personalized medicine by leveraging genetics/genomics information in current practice, such information is not yet widely available in Everyday clinical practice, and is insufficient since it only addresses one of many factors affecting response to medication. Large-scale longitudinal observation data such as Electronic Health Records (EHRs) contains millions of patient records and thus, provides a unique opportunity to reassess the effects of a drug from many different perspectives. For example, a new area of research has emerged to find both the positive effect of drugs that are already in use in terms of their ability in reducing the laboratory test measurement, and the negative effect of those drugs by assessing the potential risks of causing adverse drug reactions (ADRs).

Most of the existing studies aim to apply a linear model to estimate drug effects for a certain type of outcome of interest such as decreased cancer risk, decreased fasting blood glucose, increased risk of ADRs. These models consider all drugs simultaneously into a linear fixed effect model to account for the effect of confounders. They also leverage the longitudinal patient data using patient's own previous drug responses as control, hence these methods are called Self-Controlled Case Series (SCCS) model. Recently, a baseline regularization model has been proposed to utilize the drug histories over time using a baseline parameter in the model which can account for the variations of laboratory test results (the outcome of interest) among different patients. However, none of these studies can handle the patient heterogeneity and estimate personalized drug effects. In EHRs, there exist huge amount of variations among the patients' characteristics and their ability to respond to a drug. For example, certain group of patients with chronic health conditions can respond to a drug in a certain manner than another group of patient with a different set of chronic health conditions. Such patient heterogeneity needs to be taken into account while identifying drug effects, so that the obtained drugs with possible therapeutic indications and/or ADRs can be applied in more personalized manner during clinical decision making.

The illustrative embodiments propose a personalized drug response prediction model to identify unique response patterns of each individual patient using the longitudinal patient record. In particular, the model uses separate parameters for each individual patient which represent the drug effects on an outcome of interest. The model accounts for patient heterogeneity while building predictive models for identifying drug effects. The illustrative embodiments provide the following:

A linear model that can account for the patients' heterogeneity in terms of how they respond to a particular set of drugs, which generalizes the original baseline regularization model.

Several regularization schemes as additional loss functions, so that over parameterization of personalized drug response model can be avoided. Using one such network regularization approach, the model can further cluster the patients automatically into multiple coherent groups.

An iterative gradient descend based approach for solving the convex optimization problem.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism," Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
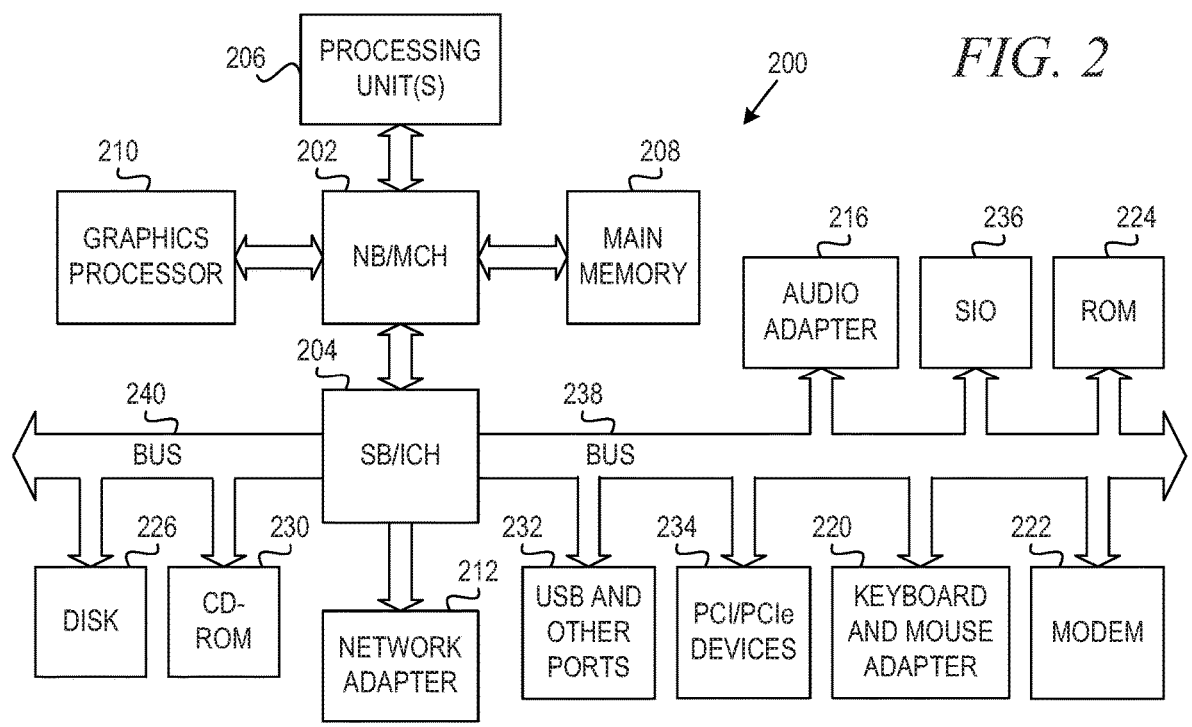
FIG. 2 is a block diagram of an example data processing system in which aspects of the illustrative embodiments are implemented.
Figure 3:
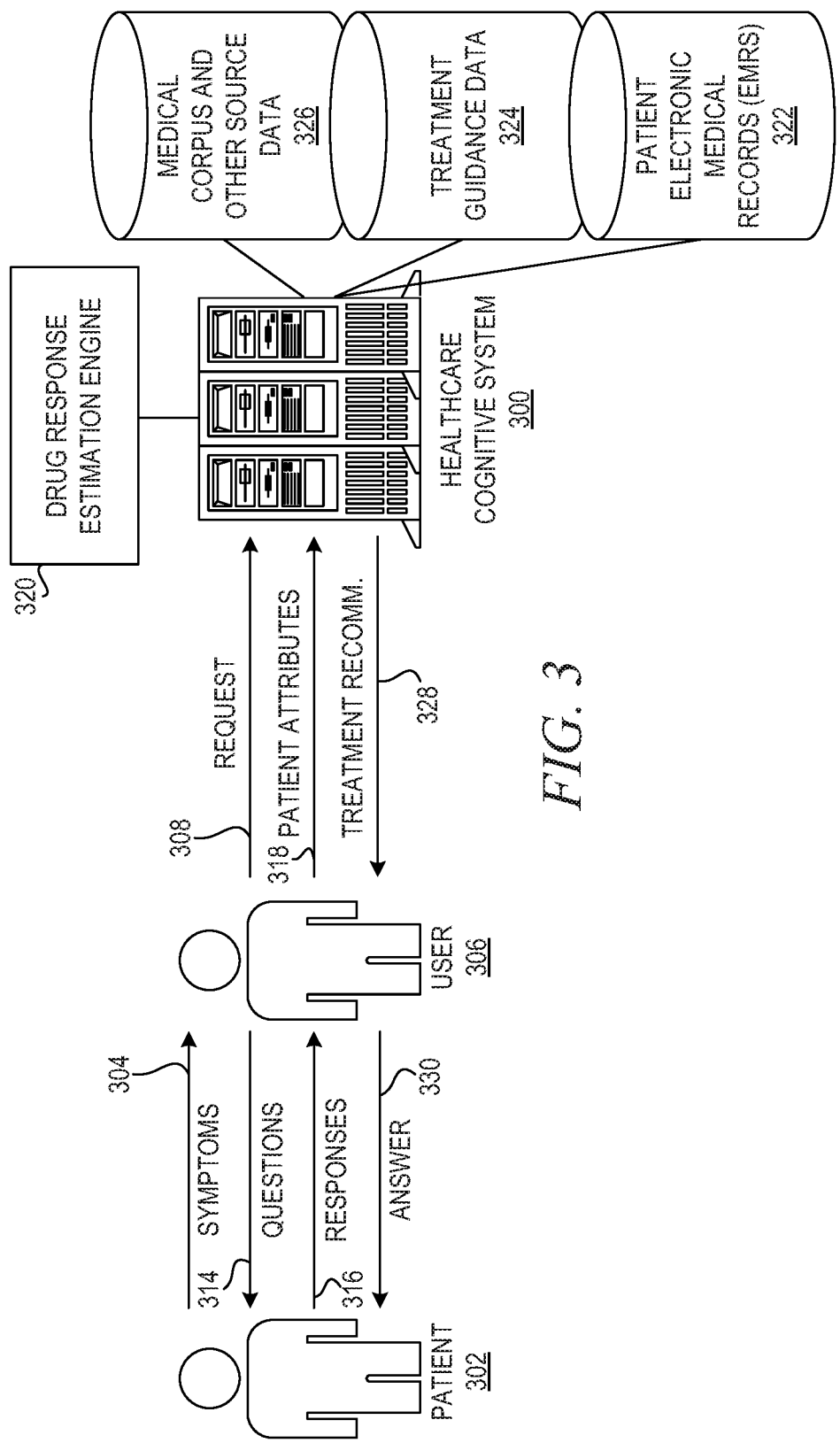
FIG. 3 is an example diagram illustrating an interaction of elements of a healthcare cognitive system in accordance with one illustrative embodiment.

As noted above, the present invention provides mechanisms for estimating personalized drug responses from real-world evidence. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for estimating personalized drug response from real-world evidence.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different, types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?" the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to estimating personalized drug responses from real-world evidence.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106. The pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and Which may process requests for such healthcare operations via the request processing pipeline 108 input as either structured or unstructured requests, natural language input questions, or the like. In one illustrative embodiment, the cognitive system 100 implements a drug response estimation engine 120.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a drug response estimation engine 120.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Flub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine What is being requested and the criteria upon which the request is to be generated as identified by the patient attributes 318, and may perform various operations for generating queries that are sent to the data sources 322-326 to retrieve data, generate candidate treatment recommendations answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to include a drug response estimation engine 320. In this embodiment, drug response estimation engine 320 uses patient demographics and diagnoses for building a patient similarity network. Drug response estimation engine 320 uses that patient similarity network for regularizing the baseline regularization framework via network LASSO regression analysis. Drug response estimation engine 320 also optimizes the parameters of the framework by learning from observed patients in the real-world evidence to assess the responses of drugs on each patient. Drug response estimation engine 320 interprets the obtained parameters for drug response and groups of patients to identify associations between a patient's demographic and comorbidities with the drug response (both therapeutic effects and adverse drug reactions). Drug response estimation engine 320 uses baseline regularization framework with optimized parameters for predicting the drug response for each patient and for each time point of the real-world evidence.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention. It should be appreciated, however, that at no time should the treatment itself be administered to the patient 302 without prior approval of the healthcare professional treating the patient, i.e. final determinations as to treatments given to a patient will always fall on the healthcare professional with the mechanisms of the illustrative embodiments serving only as an advisory tool for the healthcare professional (user 306) and/or patient 302.

As mentioned above, the healthcare cognitive system 300 may include a request processing pipeline, such as request processing pipeline 108 in FIG. 1, which may be implemented, in some illustrative embodiments, as a Question Answering (QA) pipeline. The QA pipeline may receive an input question, such as "what is the appropriate treatment for patient P?" or a request, such as "diagnose and provide a treatment recommendation for patient P."

The illustrative embodiments provide a mechanism for making predictions about drug responses for each patient separately to provide key insights and generate hypotheses about personalized therapeutic effects and adverse drug reactions. Examples of predicted associations include: 1) drug responses for each patient for each specific time; 2) potential hypotheses about new therapeutic effects and adverse drug reactions; and 3) associations between patients' characteristics and demographics with the obtained drug responses. This could be applied to pharmacovigilance risk management, keeping patients with characteristics suggesting they are especially at-risk for an adverse drug reaction (ADR) safe while, for those patient segments that do not have those characteristics, maintaining access to the recommended drug treatments.

The illustrative embodiments propose a personalized drug response estimation engine to identify unique response patterns of each individual patient using the longitudinal patient record. In particular, the personalized drug response estimation engine uses separate parameters for each individual patient which representing the drug effects on an outcome of interest.

The illustrative embodiments introduce a linear model that can account for the patients' heterogeneity in terms of how they respond to a particular set of drugs, which generalizes the original baseline regularization model.

The illustrative embodiments incorporate several regularization schemes as additional loss functions, so that over-parameterization of personalized drug response model can be avoided. Using one such network regularization approach, the personalized drug response estimation engine can further cluster the patients automatically into multiple coherent groups. The personalized drug response estimation engine uses an iterative gradient descend based approach for solving the convex optimization problem.

Figure 4A:
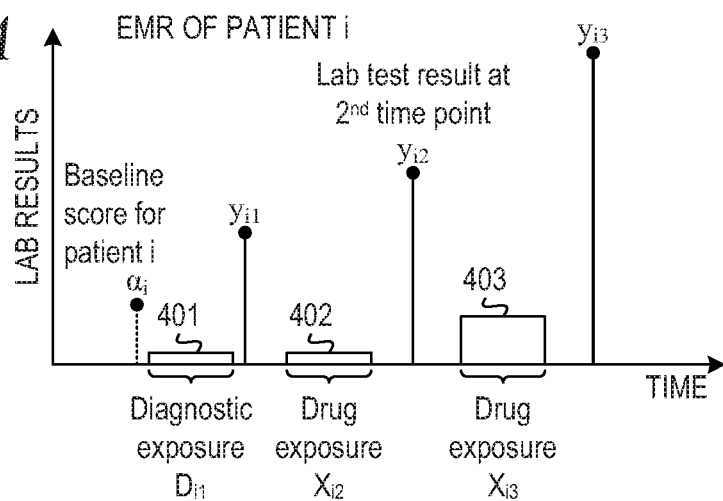
FIGS. 4A and 4B are graphs illustrating a longitudinal patient history of drug exposures in accordance with an illustrative embodiment.
Figure 4B:
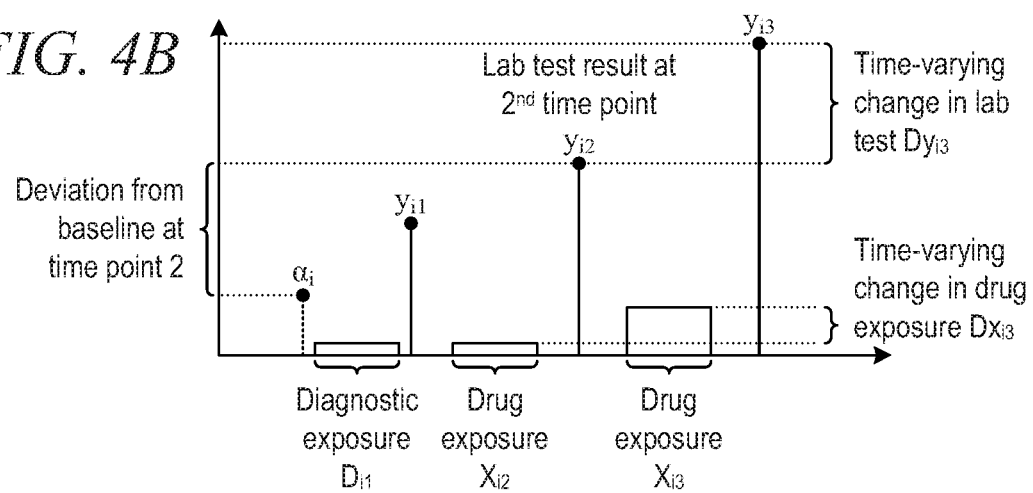

FIGS. 4A and 4B are graphs illustrating a longitudinal patient history of drug exposures in accordance with an illustrative embodiment. An example of the longitudinal patient's record is represented in FIG. 4A. Assume that there are N patients in the EHR data with at least one record of the lab test measurement under consideration. Here, denote $y_{ij} \in \mathbb{R}$ as the lab test measurement of the $i^{th}$ patient, where $i \in \{1, 2, \ldots, N\}$, at the $j^{th}$ time point taken among a total number of $j_i$ lab test measurement, i.e., $j \in \{1, 2, \ldots, j_i\}$. Also denote the drug exposures of M drugs for $i^{th}$ patient until the $j^{th}$ time point as a vector $x_{ij} \in \mathbb{R}^M$. Each entry of this vector, $x_{ijm}$ represents the response of the $m^{th}$ drug for $m \in \{1, 2, \ldots, M\}$.

Also represent the diagnostic codes for patient i at time point j also with a binary variable $D_{ijd} \in \mathbb{R}^D$ for the d-th ICD-9 diagnostic variables coming from a total number of D diagnostic codes. Also denote the demographic information available for each patient i as $G_i \in \mathbb{R}^G$ for total number of G demographic information.

The outcome of interest for each patient i is shown in the y-axis as denoted by $y_{ij}$ at $j^{th}$ time point. In FIG. 4A, box 401 represents the diagnostic exposure and boxes 402, 403 represent the drug exposures of the same patient at different time points. Also, the $\alpha_i$ represents the inherent baseline amount of outcome of interest for the same patient, without being exposed to drugs. This is to handle the inherent variations among patients in terms of their baseline amount of certain clinical outcome of interest (e.g., laboratory test measurements, cholesterol level, etc.), due to their unobserved but fixed confounder factors such as their genetic background and demographic background. The goal of illustrative embodiments can be illustrated using the right panel of the following figure.

As shown in FIG. 4B, the illustrative embodiments assess the effect of change in drug exposures ($Dx_{ij}$) due to the change in the test of lab test results ($Dy_{ij}$) that are beyond the baseline amount of laboratory measurement ($\alpha_i$) for each patient i at each time point j. This will lead to learn the personalized drug effect for each individual patient on the outcome of interest.

Most of the self-controlled case series (SCCC) model assumes that the measurement level of a patient obtained at a particular time is influenced by the joint effect of the baseline laboratory test measurement and the exposures of drugs that, the patient took until that time point. The intuition behind the incorporating the baseline effect for each individual patient is to address the issue of existing variations among different patient groups for a particular laboratory results due to their inherent predisposition towards certain clinical condition (e.g., south Asian population have higher level of lipid profiles). Besides such time-invariant baseline effect, the baseline effect present among the laboratory test measurements can also vary across time periods for each patient. Indeed, many confounding factors, both unobserved (e.g., co-morbid conditions) and observed (e.g., age or weight gains) can alter the laboratory responses of otherwise healthy subjects significantly over such a long period of observations irrespective of the drug exposure. The effects of drug response, $x_{ij}$, towards the laboratory results, $y_{ij}$, including both time-invariant and time-variant baselines, can be modeled using a fixed effect model as follows:

$$y_{ij} \mid x_{ij} = \alpha_i + t_{ij} + w^T x_{ij} + \varepsilon_{ij}, \varepsilon_{ij} \overset{i.i.d.}{\sim} N(0, \sigma^2)$$

where, $$w = [w_1 \ w_2 \ \ldots \ w_M]^T, x_{ij} = [x_{ij1} \ x_{ij2} \ \ldots \ x_{ijM}]^T,$$

Here, $\alpha_i \in \mathbb{R}$ is the patient specific unobserved and time-invariant parameter representing the baseline effect of $i^{th}$ patient on the laboratory test measurements $y_{ij}$, irrespective of time point j, drug exposures $x_{ij}$ and other patients, w is an m-1 vector with values of $w_m$, $m \in \{1, 2, \ldots, M\}$, which represents the effect of $m^{th}$ drug on the measurement of lab test. $\varepsilon_{ij}$ represents the independent and identically distributed Gaussian noises with zero means and variance $\sigma^2$. The model also includes a time-dependent parameter $t_{ij}$ which captures the deviation of the measurement at $j_{th}$ point of $i^{th}$ patient from the baseline effect $\alpha_i$.

which leads to solving the following least square problem:

$$\underset{\alpha, w, t}{\operatorname{argmin}} \frac{1}{2} \left\| y - [S \ X \ I] \begin{bmatrix} \alpha \\ w \\ t \end{bmatrix} \right\|_2^2$$

where, $$\alpha = [\alpha_1 \ \alpha_2 \ \ldots \ \alpha_N]^T,$$

$$y = [y_{11} \ \ldots \ y_{1J_1} \ \ldots \ y_{N1} \ \ldots \ y_{NJ_N}]^T,$$

$$X = [x_{11} \ \ldots \ x_{1J_1} \ \ldots \ x_{N1} \ \ldots \ x_{NJ_N}]^T,$$

$$S = \operatorname{diag}(1_1, 1_2, \ldots, 1_N),$$

$$t = [t_{11} \ \ldots \ t_{1J_1} \ \ldots \ t_{N1} \ \ldots \ t_{NJ_N}]^T.$$

Here, the mechanism stacks all lab test measurements of all patients into a column vector y with the dimension of J×1, where J is the total number of lab test measurements from all patients, i.e., $$J = \sum_{i=1}^{N} J_i.$$

Similarly, all the drug exposures are summarized in the matrix $X \in \mathbb{R}^{J \times M}$. Also, S is a block diagonal matrix with the dimension of J×N, where $1_i$ is a $J_i \times 1$ vector with all components being 1. $\alpha$ can represent the baseline non-random baseline laboratory measurements of all patients. Also, $I_{J \times J}$ is the identity matrix and both $\alpha$ and t are nuisance parameters, which have to be learned from the observed data.

The above mentioned fixed-effect model can only estimate the baseline non-random effect of the laboratory test measurements for each person, but these methods cannot model the individual responses of each patients towards the drug exposure. The objective of our method is to find the personalized drug responses that are associated with laboratory test measurement $y_{ij}$ that are beyond the patient specific baseline laboratory results, so that individual drug responses can be utilized for more refined decision making yielding personalized medicine. In this paper, we extend the fixed effect models for estimating such personalized drug effect, hence the name of the model is Personalized Drug Effectiveness Prediction (PerDREP). The unique assumption of this model is that there exist variations not only among the baseline measurements of laboratory results, but also among the effect of drug exposures on the laboratory test measurements for a particular patient due to patient heterogeneity.

The linear fixed effect model can be reformulated as below using one parameter to model the effect of one drug on one particular patient:

$$y_{ij} \mid x_{ij} = \alpha_i + t_{ij} + w_i^T x_{ij} + \varepsilon_{ij}, \varepsilon_{ij} \overset{i.i.d.}{\sim} N(0,\sigma^2)$$

where, $$W = [\, w_1 \quad w_2 \quad \ldots \quad w_N \,],$$

$$w_i = [\, w_{i1} \quad w_{i2} \quad \ldots \quad w_M \,]^T.$$

Here, the individual response of the $i^{th}$ patient on $m^{th}$ drug is denoted by $w_{im}$, where $i \in [1, 2, \ldots, N]$ and $m \in [1, 2, \ldots, M]$. So, in these models, both $w_i$ and $\alpha_i$ are patient-specific, but unknown time-invariant parameters representing the patient-specific effect of drug exposures and the baseline measurement of the laboratory test measurement. In order to solve this problem using linear least square formulation, the illustrative embodiment vectorizes the drug response matrix W into a column vector $w=[w_1^T \ldots w_N^T]^T$ with the dimension of NM×1. The illustrative embodiment also rearranges the feature matrix X of equation into a new matrix $Z=[Z_1 \; Z_2 \; \ldots \; Z_M]^T$ where $Z_m$ is a block diagonal matrix containing all the drug exposures of drug m as below:

$$Z_m = \begin{bmatrix} z_{1m} & & & \\ & z_{2m} & & \\ & & \ddots & \\ & & & z_{Nm} \end{bmatrix}_{J \times N},$$

$$z_{im} = [\, x_{i1m} \quad x_{i2m} \quad \ldots \quad x_{iJ_i m} \,]^T.$$

So, if one substitutes all $Z_m$ corresponding to all drugs $m \in [1, 2, \ldots, M]$, the new feature matrix Z can be obtained with the dimension of J×NM:

$$Z = \begin{bmatrix} z_{11} & & z_{1M} & \\ & z_{21} & \cdots & z_{2M} \\ & & \ddots & & \ddots \\ & & & z_{N1} & & z_{NM} \end{bmatrix}.$$

The illustrative embodiment reformulates the personalization drug effectiveness prediction problem as the linear least square formulation as below:

$$\operatorname*{argmin}_{\alpha, W} \mathcal{L}_1(\alpha, W) = \operatorname*{argmin}_{\alpha, W, t} \frac{1}{2} \left\| y - [S \; Z \; I] \begin{bmatrix} \alpha \\ W \\ t \end{bmatrix} \right\|_2^2.$$

This least square regression problem has total number of J samples, however, the model complexity increases as it has to learn MN+N+J parameters. In order to avoid over-fitting, the illustrative embodiment imposes several regularization techniques on this model as described in next few subsections.

The illustrative embodiment introduces a few assumptions to the PerDREP modes using temporal smoothness of the consecutive responses of laboratory tests of patients similar to the baseline regularization method. Without loss of generalizablity, let us consider two consecutive laboratory measurements of the patient i as $y_{ij}$ and $y_{i(j+1)}$ that were taken on day $\pi_{ij}$ and $\pi_{i(j+1)}$, respectively. Now, if the two adjacent pairs are closer in time, i.e., $\pi_{i(j+1)} - \pi_{ij} \leq \delta$ for a predefined threshold $\delta$ and the drug exposures remain constant in that period, then the changes on test measurements $y_{i(j+1)} - y_{ij}$ is due to the confounders within the time period $\delta$. Since the effect of time-varying confounders such as age do not fluctuate over a short time period, a reasonable assumption will be that the changes in the baseline effect should be small, i.e., $|(\alpha_i - t_{i(j+1)}) - (\alpha_i - t_{i(j+1)})| = |t_{i(j+1)} - t_{ij}|$ is small. Using this assumption, a regularization term can be incorporated into the model based on fused lasso penalty on the consecutive baseline parameters.

A slightly stricter assumption can be introduced in the model above by considering that the consecutive test measurements that are within $\delta$ time period have same baseline effect, i.e., $|\pi_{i(j+1)} - \pi_{ij}| \leq \delta \Rightarrow t_{ij} = t_{i(j+1)}$, for a small parameter. Then, from the above, $$E[y_{i(j+1)} - y_{ij} | x_{i(j+1)} - x_{ij}] = w_1^T (x_{i(j+1)} - x_{ij})$$

where, all the nuisance parameters are eliminated and the change in the laboratory test measurements only depend on the W, therefore, reduces the number of parameters to be estimated drastically into MN. Note that although this types of model adopt stricter assumptions on baseline parameters with fewer parameters than the fused lasso based baseline regularization approach, they still achieve almost similar performances to the baseline regularization approach. This was demonstrated in a non-personalized fixed-effect model. Since the main focus of the illustrative embodiment is on learning a personalized drug response prediction from large-scale EHR data, we adopt the stricter assumptions in our model without loss of efficiency.

Given this assumption, we can reformulate our learning problem as learning the effect of changes of consecutive output given any changes of drug exposure. This is illustrated in FIG. 4B, where the change of two consecutive test measures is modeled as the direct response to the changes in drug intakes, since the baselines did not change within the $\delta$ time period.

Now, one can construct a cohort by considering only those patients that have at least one pair of two consecutive laboratory test measurements within the time period. Note that this cohort will also solve the issue of irregularities in temporal dimension as described earlier. In this cohort, one can reformulate the linear learning problem as follows:

$$\operatorname*{argmin}_{W} \mathcal{L}_1(W) = \operatorname*{argmin}_{W} \frac{1}{2} \| D^\delta y - D^\delta Z W \|_2^2.$$

Here, $D^\delta$ is a sparse matrix with dimension s×J containing only 0 or ±1 entries, where s is the total number of consecutive pairs of test measurements that are within $\delta$ time period in the whole cohort. The purpose of $D^\delta$ is to create a first difference matrix from the observational data, i.e., when each row of $D^\delta$ is multiplied with y, the new vector will contain the difference of the later measurement from the earlier measurement. For example, difference matrix for patient i is $D_i^\delta \in \mathbb{R}^{s_i \times J}$, where $s_i$ is the total number of consecutive pairs within $\delta$ period. For each $k^{th}$ consecutive pair $<y_{ij}, y_{i(j-1)}>$ for $k \in [1, 2, \ldots, s_i]$, the corresponding row of $D_i^\delta$ will be $[0, \ldots, 0, -1, 1, 0, \ldots, 0]$ with $-1$ and $1$ in $j^{th}$ and $J^{th}$ positions respectively. Now, $$D^\delta = \text{diag}(D_1^\delta, \ldots, D_N^\delta), \text{ where } s = \sum_i s_i.$$

The least square regression problem has a total number of J samples, where the total number of MN parameters must be learned. EMR data are often high-dimensional, where large number of samples (N) are considered for a particular cohort and large number of drugs (M) prescribed for those patients with diverse diagnostic backgrounds. On the other hand, each sample contains a few number of consecutive laboratory test measurements that are within $\delta$, which still leads to over-parameterization.

To overcome above mentioned issue, the illustrative embodiment further regularizes the W, which has N rows and M columns corresponding to patients and drugs, respectively. In particular, the illustrative embodiment imposes the regularization on the drug effectiveness within each sample so that feature selection can be performed simultaneously for easier model interpretation. The easiest way to impose sparsity will be to impose $\ell_1$ penalty on all drug features of all samples as follows:

$$\mathcal{L}_2 = \lambda_1 \frac{1}{2} \sum_{i=1}^N \|w_i\|_1.$$

However, such heavy regularization on all parameters will lead to many sample weights being completely zero due to the small number of samples available in the dataset. Rather we want to select a few drugs for most of the patients, so that we can interpret the such drug effects clinically based on other properties of the patients such as diagnostic and demographic background. Therefore, the illustrative embodiment considers mixed-type regularization using both $\ell_1$ and $\ell_2$ that have been used successfully in many domains, where some predefined group structures among the variables are available. Although the definition of group is not directly applicable in our case, still we can consider each sample weight vector $w_i$ as a group (in total N groups).

In the case of high dimensional learning, the illustrative embodiment assumes that there exists intra-group sparsity, i.e., $\ell_1$ regularization is applied on the individual drug exposure features within each sample (i.e., $w_i$), while intergroup (samples) non-sparsity is achieved by imposing a $\ell_2$ structure on the parameters obtained from all samples. This type of mixed $\ell_{1,2}$ or exclusive regularization can be defined as follows:

$$\mathcal{L}_2 = \lambda_1 \frac{1}{2} \sum_{i=1}^N \|w_i\|_1^2$$

where $\lambda_1 \geq 0$ is a hyper-parameter in the model. The square of $\ell_1$ above will guarantee that all of the sample weights will remain non-zero (i.e., $w_i \neq 0$).

The linear least-square formulation further assumes the personalized drug responses of a particular patient are independent of other patient. However, this assumption is not true in EMR, because patients having similar background should have similar types of drug responses. For example, a particular group of patients with kidney failure may respond to a drug used to lower HbA1c in a different degree than the patient group with chronic heart diseases. Based on this observation, the illustrative embodiment aims to further regularize the drug responses of two patients based on their similarity in terms of their background information such as diagnostic profile, demographic backgrounds and so on.

Consider a graph $R \in \mathbb{R}^{N \times N}$, whose elements $[R]_{i,i'} = r_{ii'} \geq 0$ is a coefficient representing the relationship between each pair of patients i and i' for $i \in \{1, 2, \ldots, N\}$ and $i' \in \{1, 2, \ldots, N\}$. This graph can be computed using any similarity measure on the background information of patients i and i' such as their demographic information $G_{[i,\cdot]}$ and $G_{[i',\cdot]}$, or their diagnostic profiles $D_{[i,\cdot]}$ and $D_{[i',\cdot]}$, or both by combined the individual similarity scores. Assume here that R is an undirected graph (i.e., $R = R^T$) and the diagonal elements of R are zero, i.e., $r_{ii} = 0$ for all $i \in \{1, 2, \ldots N\}$. Based on such relatedness of a pair of patients (i and i') $r_{ii'}$, the illustrative embodiment imposes a network regularizer on the corresponding two vectors of $w_i$ and $w'_i$ as follows:

$$\mathcal{L}_3 = \lambda_2 \frac{1}{2} \sum_{i,i'=1}^N r_{i,i'} \|w_i - w'_i\|_2$$

where $\lambda_2 \geq 0$ is another regularization hyper-parameter.

If one combines all our assumptions described above, one gets the final formulation of the Personalized Drug Effectiveness Prediction model as below:

$$\operatorname*{argmin}_W \mathcal{L} = \mathcal{L}_1 + \mathcal{L}_2 + \mathcal{L}_3 =$$

$$\operatorname*{argmin}_W \|Dy - DZw\|_2^2 + \lambda_1 \sum_{i=1}^N \|w_i\|_1^2 + \lambda_2 \sum_{i>i'}^N \sum_{i'=1}^{N-1} r_{ii'} \|w_i - w_{i'}\|_2.$$

Here, $\lambda_1$ and $\lambda_2$ are the hyper-parameters. $\lambda_1$ controls the exclusive lasso penalty and $\lambda_2$ controls the network lasso penalty. More importantly, these two types of regularization when combined together can provide nice model interpretations by learning multiple local predictive models. If $\lambda_2$ is sufficiently large, then we can efficiently cluster the samples into multiple groups based on the similarities of $w'_i$s. More specifically, when $\|w_i - w_{i'}\|_2$ is too small (preferably zero), then we can consider that $i^{th}$ and $i^{th}$ patients belong to the same clusters. At the same time outliers tend to form their own clusters that are very distant from the other normal clusters in terms of their average drug response co-efficients. Furthermore, if $\lambda_1$ sparsity parameter is sufficiently large, then it helps to select multiple groups of drugs where each group of drugs can correspond locally either to an individual sample or to the corresponding duster to which the individual sample belongs.

The PerDREP problem as formulated above is a convex optimization problem where a global solution of W is available. We use a recently proposed localized lasso approach to solve such large number of parameters using an iterative least square method. One of the advantage of such localized lasso optimization problem is that it does not require any tuning parameter and guaranteed to converge to the optimal solution.

The localized lasso approach first derives some intermediate quantities based on the given design matrix Z and the relatedness graph G as follows:

$$C = \begin{bmatrix} c_{11} & \cdots & c_{1N} \\ \vdots & \ddots & \vdots \\ c_{N1} & \cdots & c_{NN} \end{bmatrix},$$

$$c_{ii'} = \begin{cases} \sum_{k=1}^{n} \frac{r_{ik}}{\|w_i - w_k\|_2} - \frac{r_{ii'}}{\|w_i - w_{i'}\|_2}, & i = i', \\ -\frac{r_{ii'}}{\|w_i - w_{i'}\|_2}, & i \neq i'. \end{cases}$$

$$F_g = I_d \otimes C, [F_e]_{ll} = \sum_{i=1}^{n} \frac{\Pi_{il} \|w_i\|_1}{\|W\|_l}, H = \lambda_1 F_g + \lambda_2 F_e.$$

Here, $F_g \in \mathbb{R}^{MN \times MN}$ is a block diagonal, $F_e \in \mathbb{R}^{MN \times MN}$ is a diagonal matrix. $I_d$ is a d×d identify matrix. $\otimes$ is the Kronecker product. $\Pi_{il}$ is an indicator representing whether the lth element in |W| belongs to $|w_i|$. However, $F_g$, $F_e$ and H themselves depend on W.

Based on these new intermediate quantities, the PerDREP optimization problem can be reformulated as optimizing the following objective function, so that W and the intermediate quantities ($F_g$, $F_e$ and H) can be optimized iteratively.

$$\mathcal{L} = \|Dy - DZW\|_2^2 + W^T(\lambda_1 F_g^{(t)} + \lambda_2 F_e^{(t)})W$$

where $F_g^{(t)}$, $F_e^{(t)}$ and H are the values of $F_g$, and $F_e$ are step t. Then, W can be estimated as follows and the process will be iterated until convergence (Algorithm 1 in FIG. 5).

$$W^{(t+1)} \leftarrow (H^{(t)})^{-1} Z^T D^T (I_n + DZ(H^{(t)})^{-1} Z^T D^T)^{-1} Dy$$

FIG. 6 is a block diagram illustrating a drug response estimation engine in accordance with an illustrative embodiment. Drug response estimation engine 610 is an overall framework that receives real-world evidence (RWE) data 601 as input and provides drug response estimations or predictions 621-623 as output. RWE data 601 may include demographics, lab tests, diagnoses, and medication history, such as data from medical corpus and other source data 326 and patient electronic medical records (EMRs) 322 in FIG. 3.

Drug response estimation engine 610 includes patient similarity network builder component 6111, which uses patient demographics and diagnoses for building a patient similarity network based on the information available prior to their drug-exposure such as the patients' background information, diagnosis history, comorbidities, etc., so that this patient network can be leveraged during learning personalized drug responses. The purpose of this patient similarity network is to make sure that similar patients will have similar drug responses to a certain outcome of interest. Therefore, this patient similarity network is leveraged in the later steps.

LASSO analysis (component 612) based regularization have been applied on the PerDREP model in two ways for ensuring model sparsity. First, the exclusive LASSO penalty ensures that the parameters learnt from the models are sparse enough, i.e., only a few parameters of drug responses of each patient are non-zero. Second, it uses network LASSO approach for the patient similarity network to regularize the two drug response parameters of two similar patient.

A statistical model is built, such as by using a regularized fixed-effect model, to leverage the patient similarity network such that drug responses for new patients may be predicted based on the statistical model. In particular LASSO regression analysis component 612 optimizes the following objective function:

$$\operatorname*{argmin}_{w} \|Dy - DZw\|_2^2 + \lambda_1 \sum_{i=1}^{N} \|w_i\|_1^2 + \lambda_2 \sum_{i>i'}^{N} \sum_{i'=1}^{N-1} r_{ii'} \|w_i - w_{i'}\|_2.$$

Here, the $w_i$ vector denotes the drug response for each individual patient i, and $r_{ii'}$ the represents the patient similarity between $i^{th}$ and $i'^{th}$ patients that is obtained from the previous step. Specifically, the similarity network of the patients is used for regularizing the corresponding two drug response vectors, $w_i$ and $w_{i'}$. The last term in the above-mentioned objective function is to make the obtained drug response features more interpretable by selecting only a few of the most important drug responses for each patient. In fact, this type of regularization will perform feature selection for each patient simultaneously. Finally, LASSO regression analysis component 612 uses the baseline regularization framework using a convex optimization framework to learn the parameters in the above mentioned objective function that predicts the drug response for each patient and for each time point of the real world evidence. Note that the learned parameters denoting drug response can be both positive and negative representing the indication and adverse drug reaction for a particular drug on a particular patient.

Patient clustering component 613 interprets the obtained parameters for drug responses and groups of patients to find associations between patient demographics and comorbidities with the drug responses. We used hierarchical clustering with K=10 with cosine similarities. The drug response estimation engine 610 provides more interpretation for personalized medicine by further analyzing the obtained drug responses of each patient ($w_i$) and the background information available from real-world evidence data for the same particular patient. Patient clustering component 613 interprets the obtained parameters for drug responses and groups of patients to identify associations between patient's demographic and comorbidities. In particular, a clustering mechanism is applied to find groups of patients that have similar drug responses and similar background information. This will provide further interpretation of the observed phenomena of the specific drug responses relating to a certain kind of diagnosis and demographic background, which can be leveraged for clinical decision making in personalized medicine.

Drug response estimation engine 610 generates significant drug responses for indications and adverse drug reactions (ADRs) 621. The significant drug responses can be obtained by considering the non-zero co-efficient ($w_i$) of drug response parameter.

Drug response estimation engine 610 also generates significant drug responses in patient groups 622. These groups are the patients with similar drug responses for a particular laboratory test measurement, e.g., HbA1C for measuring the treatment of hyperglycemia.

Drug response estimation engine 610 generates drug response predictions 623. In this prediction, the average drug responses are recorded for each group as well.

Figure 7:
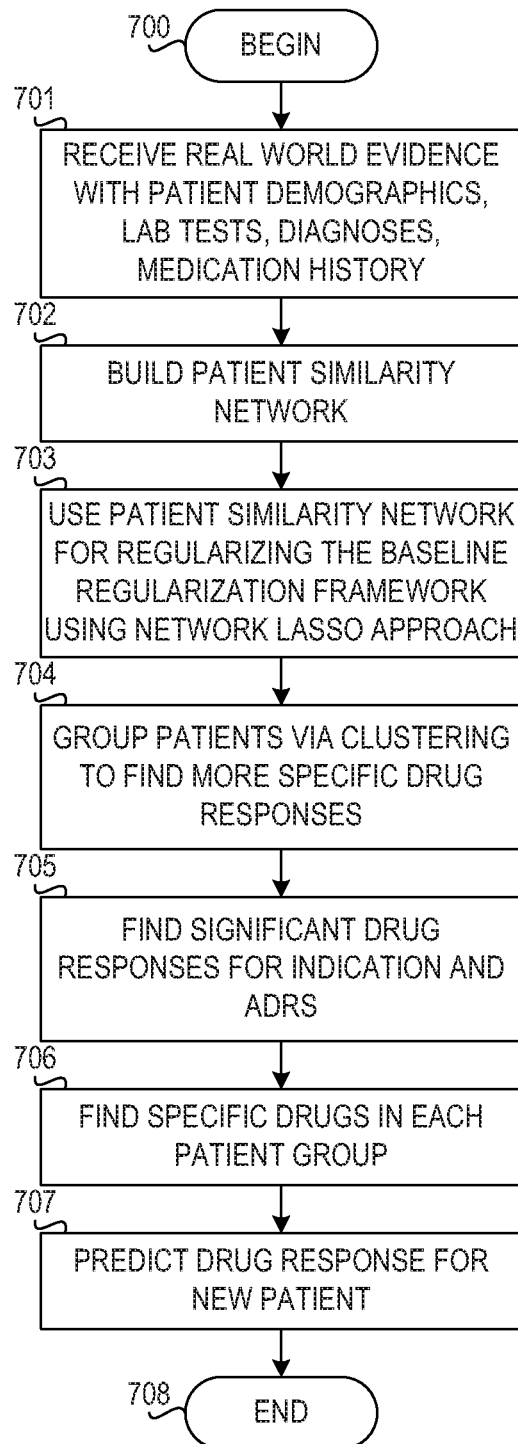
FIG. 7 is a flowchart illustrating operation of a drug response estimation engine in accordance with an illustrative embodiment.

FIG. 7 is a flowchart illustrating operation of a drug response estimation engine in accordance with an illustrative embodiment. Operation begins (block 700), and the drug response estimation engine receives real-world evidence with patient demographics, lab tests, diagnoses, and medication history (block 701). The drug response estimation engine builds a patient similarity network (block 702). The drug response estimation engine uses the patient similarity network for regularizing the baseline regularization framework using a network localized LASSO approach (block 703). The drug response estimation engine then groups patients via clustering to find more specific drug responses (block 704).

Next, the drug response estimation engine finds significant drug responses for indication and adverse drug responses (block 705). The drug response estimation engine finds specific drug responses in each patient group (block 706). The drug response estimation engine also predicts drug responses for a new individual patient (block 707). Thereafter, operation ends (block 708).

Thus, the illustrative embodiments provide a mechanism to identify responses of drugs on a specific patient based on patient's demographics, diagnostics, lab tests, and medication history from real world evidence. Compared to known solutions, the system has the following main advantages: (1) learns personalized drug responses for each individual patient from the real world evidence data; (2) effectively exploits the patients' demographic background information and prior history for comorbidities; (3) predicts both types of personalized drug responses—positive (i.e., therapeutic effects) and negative (i.e., adverse drug reactions) for each patient; and (4) provides interpretations of the drug responses by mapping them with patients' background demographics and diagnostics.

As noted above, it should be appreciated that the illustrative embodiments may take the form of an entirely hardware embodiment, an entirely software embodiment or an embodiment containing both hardware and software elements, in one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a drug response estimation engine, wherein the drug response estimation engine operates to:

receive, by the drug response estimation engine, real-world evidence for a plurality of patients;

build a drug response matrix, W, representing an individual response of each patient on each drug, vectorized into a column vector, w, a column matrix of laboratory test measurements, y, and a block diagonal matrix, Z, of drug exposures based on information in the real-world evidence;

build, by the regression analysis component, a statistical model using a network localized regression analysis approach, wherein building the statistical model comprises using a difference matrix to determine a difference in test measurements over time and a difference in drug exposures over time based on the column matrix of laboratory test measurements, the block diagonal matrix of drug exposures, and the drug response matrix, wherein the statistical model learns parameters that predict drug responses for each patient and for each time point of the real-world evidence;

group, by a patient clustering component executing within the drug response estimation engine, patients based on demographics and comorbidities to form a plurality of patient groups, wherein the patient clustering component groups the patients using the learned parameters that predict drug responses such that each patient group within the plurality of patient groups represents patients that have similar drug responses and background information;

estimate, by the drug response estimation engine, drug responses for a given patient based on the statistical model and the plurality of patient groups; and output, by the drug response estimation engine, the drug responses for the given patient.

2. The method of claim 1, wherein the real-world evidence comprises at least one of patient demographics, lab tests, diagnoses, or medication history.

3. The method of claim 1, wherein estimating drug responses comprises estimating significant drug responses for indication and adverse drug reactions.

4. The method of claim 1, wherein estimating drug responses comprises estimating specific drug responses in each patient group within the plurality of patient groups.

5. The method of claim 4, wherein each patient group comprises patients with similar drug responses for a particular laboratory test measurement.

6. The method of claim 1, wherein estimating drug responses comprises recording average drug responses for each group within the plurality of patient groups.

7. The method of claim 1, wherein estimating drug responses comprises generating predicted associations including at least one of drug responses for each patient for each specific time, potential hypotheses about new therapeutic effects and adverse drug reactions, or associations between the given patients' characteristics and demographics with the obtained drug responses.

8. The method of claim 1, wherein the statistical model optimizes the following objective function:

$$\operatorname*{argmin}_{W} \|Dy - DZw\|_2^2 + \lambda_1 \sum_{i=1}^{N} \|w_i\|_1^2 + \lambda_2 \sum_{i>i'}^{N} \sum_{i'=1}^{N-1} r_{ii'} \|w_i - w_{i'}\|_2$$

wherein D is a difference matrix, y is a column matrix of laboratory test measurements, Z is a block diagonal matrix of drug exposures, w is a drug response vector, wherein $\lambda_1$ is a hyper-parameter that controls an exclusive lasso penalty and $\lambda_2$ is a hyper-parameter that controls a network lasso penalty, wherein $w_i$ is a vector that denotes a drug response for each individual patient i, and wherein $r_{ii'}$ represents a patient similarity between the $i^{th}$ and $i'^{th}$ patients.

9. A computer program product comprising a non-transitory computer readable storage medium having a computer readable program stored therein, wherein the computer readable program, when executed on at least one processor of a data processing system, causes the data processing system to implement a drug response estimation engine, wherein the computer readable program causes the data processing system to:

receive, by the drug response estimation engine, real-world evidence for a plurality of patients;

build a drug response matrix, W, representing an individual response of each patient on each drug, vectorized into a column vector, w, a column matrix of laboratory test measurements, y, and a block diagonal matrix, Z, of drug exposures based on information in the real-world evidence;

build, by the regression analysis component, a statistical model using a network localized regression analysis approach, wherein building the statistical model comprises using a difference matrix to determine a difference in test measurements over time and a difference in drug exposures over time based on the column matrix of laboratory test measurements, the block diagonal matrix of drug exposures, and the drug response matrix, wherein the statistical model learns parameters that predict drug responses for each patient and for each time point of the real-world evidence;

group, by a patient clustering component executing within the drug response estimation engine, patients based on demographics and comorbidities to form a plurality of patient groups, wherein the patient clustering component groups the patients using the learned parameters that predict drug responses such that each patient group within the plurality of patient groups represents patients that have similar drug responses and background information;

estimate, by the drug response estimation engine, drug responses for a given patient based on the statistical model and the plurality of patient groups; and output, by the drug response estimation engine, the drug responses for the given patient.

10. The computer program product of claim 9, wherein the real-world evidence comprises at least one of patient demographics, lab tests, diagnoses, or medication history.

11. The computer program product of claim 9, wherein estimating drug responses comprises estimating significant drug responses for indication and adverse drug reactions.

12. The computer program product of claim 9, wherein estimating drug responses comprises estimating specific drug responses in each patient group within the plurality of patient groups.

13. The computer program product of claim 12, wherein each patient group comprises patients with similar drug responses for a particular laboratory test measurement.

14. The computer program product of claim 9, wherein estimating drug responses comprises recording average drug responses for each group within the plurality of patient groups.

15. The computer program product of claim 9, wherein the statistical model optimizes the following objective function:

$$\operatorname*{argmin}_{W} \|Dy - DZw\|_2^2 + \lambda_1 \sum_{i=1}^{N} \|w_i\|_1^2 + \lambda_2 \sum_{i>i'}^{N} \sum_{i'=1}^{N-1} r_{ii'} \|w_i - w_{i'}\|_2$$

wherein D is a difference matrix, y is a column matrix of laboratory test measurements, Z is a block diagonal matrix of drug exposures, w is a drug response vector, wherein $\lambda_1$ is a hyper-parameter that controls an exclusive lasso penalty and $\lambda_2$ is a hyper-parameter that controls a network lasso penalty, wherein $w_i$ is a vector that denotes a drug response for each individual patient I, and wherein $r_{ii'}$ represents a patient similarity between the $i^{th}$ and $I'^{th}$ patients.

16. An apparatus comprising:

a processor; and a memory coupled to the processor, wherein the memory comprises instructions which, when executed by the processor, cause the processor to implement a drug response estimation engine, wherein the instructions cause the processor to:

receive, by the drug response estimation engine, real-world evidence for a plurality of patients;

build a drug response matrix, W, representing an individual response of each patient on each drug, vectorized into a column vector, w, a column matrix of laboratory test measurements, y, and a block diagonal matrix, Z, of drug exposures based on information in the real-world evidence;

build, by the regression analysis component, a statistical model using a network localized regression analysis approach, wherein building the statistical model comprises using a difference matrix to determine a difference in test measurements over time and a difference in drug exposures over time based on the column matrix of laboratory test measurements, the block diagonal matrix of drug exposures, and the drug response matrix, wherein the statistical model learns parameters that predict drug responses for each patient and for each time point of the real-world evidence;

group, by a patient clustering component executing within the drug response estimation engine, patients based on demographics and comorbidities to form a plurality of patient groups, wherein the patient clustering component groups the patients using the learned parameters that predict drug responses such that each patient group within the plurality of patient groups represents patients that have similar drug responses and background information;

estimate, by the drug response estimation engine, drug responses for a given patient based on the statistical model and the plurality of patient groups; and output, by the drug response estimation engine, the drug responses for the given patient.

17. The apparatus of claim 16, wherein the real-world evidence comprises at least one of patient demographics, lab tests, diagnoses, or medication history.

18. The apparatus of claim 16, wherein estimating drug responses comprises estimating significant drug responses for indication and adverse drug reactions.

19. The apparatus of claim 16, wherein estimating drug responses comprises estimating specific drug responses in each patient group within the plurality of patient groups, wherein each patient group comprises patients with similar drug responses for a particular laboratory test measurement.

20. The apparatus of claim 16, wherein the statistical model optimizes the following objective function:

$$\underset{W}{\operatorname{argmin}} \|Dy - DZw\|_2^2 + \lambda_1 \sum_{i=1}^{N} \|w_i\|_1^2 + \lambda_2 \sum_{i>i'}^{N} \sum_{i'=1}^{N-1} r_{ii'} \|w_i - w_{i'}\|_2$$

wherein D is a difference matrix, y is a column matrix of laboratory test measurements, Z is a block diagonal matrix of drug exposures, w is a drug response vector, wherein $\lambda_1$ is a hyper-parameter that controls an exclusive lasso penalty and $\lambda_2$ is a hyper-parameter that controls a network lasso penalty, wherein $w_i$ is a vector that denotes a drug response for each individual patient i, and wherein $r_{ii'}$ represents a patient similarity between the $i^{th}$ and $i'^{th}$ patients.

* * * * *